US008167791B2

(12) United States Patent
Tanaka

(10) Patent No.: US 8,167,791 B2
(45) Date of Patent: May 1, 2012

(54) ENDOSCOPE SYSTEM

(75) Inventor: Hideki Tanaka, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/782,983

(22) Filed: May 19, 2010

(65) Prior Publication Data
US 2010/0298641 A1 Nov. 25, 2010

Related U.S. Application Data

(63) Continuation of application No. PCT/JP2009/067555, filed on Oct. 8, 2009.

(30) Foreign Application Priority Data

Jan. 15, 2009 (JP) .................. 2009-007024

(51) Int. Cl.
*A61B 1/04* (2006.01)
*A61B 1/00* (2006.01)
(52) U.S. Cl. ......... 600/117; 600/109; 600/118; 600/146
(58) Field of Classification Search .................. 600/117, 600/424, 118, 109, 921, 146, 150; 382/128
See application file for complete search history.

(56) References Cited

U.S. PATENT DOCUMENTS

| 5,036,464 A | * | 7/1991 | Gillies et al. .................. 600/145 |
| 5,269,289 A | * | 12/1993 | Takehana et al. ............. 600/109 |
| 5,347,987 A | | 9/1994 | Feldstein et al. |
| 5,469,254 A | * | 11/1995 | Konomura ................. 356/241.1 |
| 5,469,840 A | * | 11/1995 | Tanii et al. ..................... 600/117 |
| 5,658,238 A | * | 8/1997 | Suzuki et al. .................. 600/150 |
| 7,828,721 B2 | * | 11/2010 | Kumei et al. ................. 600/109 |
| 2007/0173694 A1 | * | 7/2007 | Tsuji et al. ..................... 600/146 |

FOREIGN PATENT DOCUMENTS

| EP | 2 008 571 A1 | 12/2008 |
| GB | 2 238 440 A | 5/1991 |
| JP | 03-165732 | 7/1991 |
| JP | 05-228102 | 9/1993 |
| JP | 07-155289 | 6/1995 |
| JP | 2005-157902 | 6/2005 |

OTHER PUBLICATIONS

International Search Report dated Dec. 15, 2009.
Extended European Search Report dated Jun. 17, 2011 in counterpart European Patent Application No. EP 09838350.8.

* cited by examiner

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

An endoscope system of the present invention includes an image pickup section that picks up an image of an object, a position detection section that detects a position indicating a predetermined object in the image of the object obtained by the image pickup section and a probability calculation section that calculates a probability value as a degree indicating accuracy of the position being the predetermined object using first information obtained from the image and second information on a condition of the object whose image is picked up by the image pickup section.

18 Claims, 9 Drawing Sheets

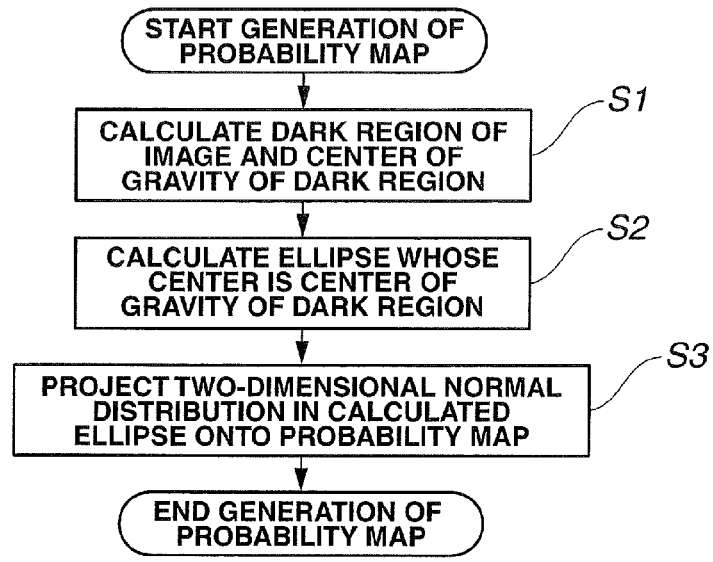
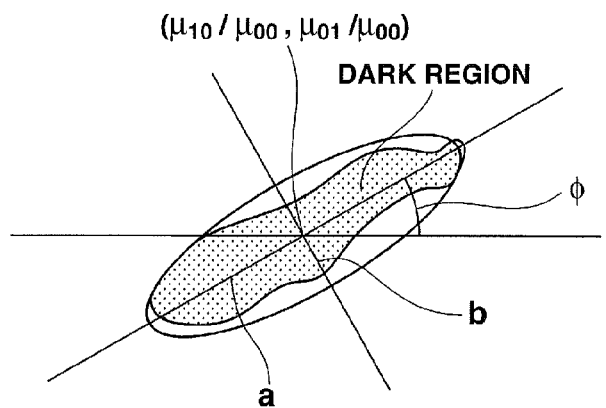
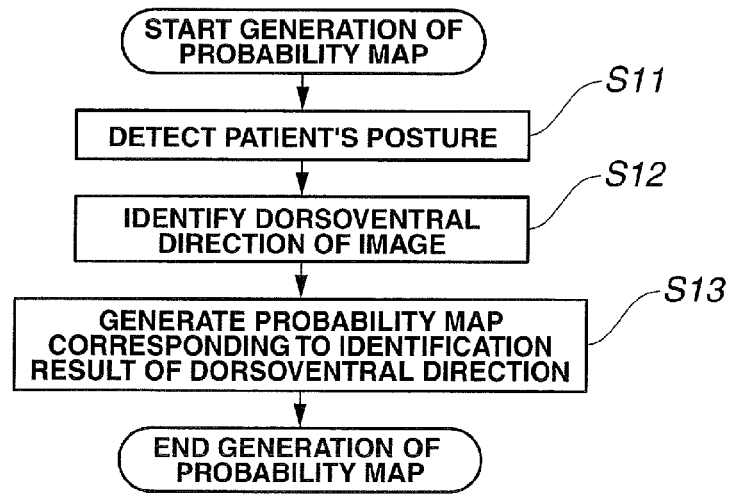

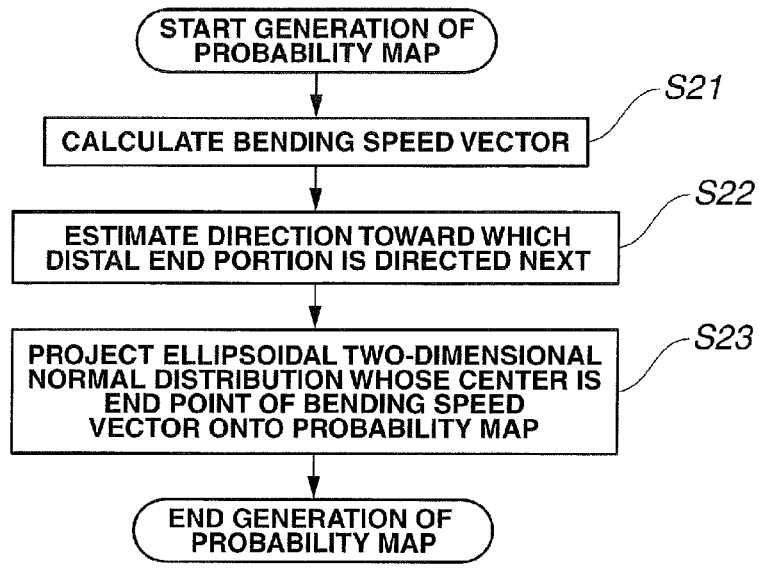
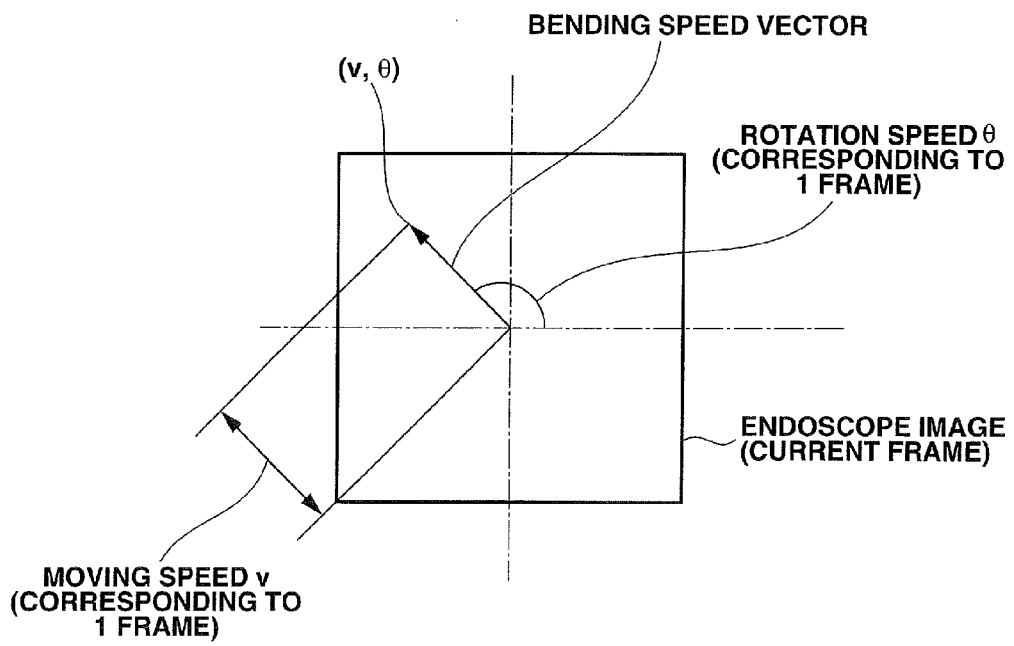

ENDOSCOPE SYSTEM

CROSS REFERENCE TO RELATED APPLICATION

This application is a continuation application of PCT/JP2009/067555 filed on Oct. 8, 2009 and claims benefit of Japanese Application No. 2009-007024 filed in Japan on Jan. 15, 2009, the entire contents of which are incorporated herein by this reference.

FIELD OF THE INVENTION

The present invention relates to an endoscope system, and more particularly, to an endoscope system capable of supporting insertion of an endoscope into an object to be examined such as a body cavity.

DESCRIPTION OF THE RELATED ART

Endoscopes are conventionally widely used in the medical field and industrial field or the like, and, for example, in the medical field, endoscopes are used to perform observation and various kinds of treatment on living tissue or the like in the body cavity.

Furthermore, Japanese Patent Application Laid-Open Publication No. 7-155289 discloses a technique of setting a target position (moving direction and amount of movement) as appropriate when extracting a dark region in an observed image obtained by an endoscope and inserting the endoscope in such a way that the center position of the dark region matches the center position of the observed image.

SUMMARY OF THE INVENTION

An endoscope system according to the present invention includes an image pickup section that picks up an image of an object, a position detection section that detects a position indicating a predetermined object in the image of the object obtained by the image pickup section and a probability calculation section that calculates a probability value as a degree indicating accuracy of the position being the predetermined object using first information obtained from the image picked up by the image pickup section and second information on a condition of the object whose image is picked up by the image pickup section.

An endoscope system according to the present invention includes an endoscope provided with an insertion portion inserted into a body cavity and an image pickup section provided at a distal end portion of the insertion portion, a position setting section that sets a target position through which the distal end portion is made to pass in an image of an object obtained by the image pickup section and a probability calculation section that calculates a probability value as a degree indicating accuracy of the position being the predetermined object using first information obtained from the image picked up by the image pickup section and second information on a condition of the object whose image is picked up by the image pickup section.

An endoscope system according to the present invention includes an image pickup section that picks up an image of an object, a position detection section that detects a position indicating a predetermined object in the image of the object obtained by the image pickup section, a pixel feature value calculation section that acquires a plurality of pixel feature values from the image and a probability calculation section that calculates a probability value as a degree indicating accuracy of the position being the predetermined object based on the plurality of pixel feature values.

An endoscope system according to the present invention includes an image pickup section that moves inside an object to be examined and acquires an image of an object in the object to be examined, an extraction section that extracts a dark region in an image corresponding to the image of the object, an information acquisition section that acquires predetermined information different from the extraction result of the dark region by the extraction section and a probability calculation section that calculates a probability value indicating accuracy as a passage target position of the image pickup section using the extraction result of the dark region by the extraction section and the predetermined information.

An endoscope system according to the present invention includes an endoscope provided with an insertion portion inserted into a body cavity of an object to be examined and an image pickup section provided at a distal end portion of the insertion portion to acquire an image of an object in the body cavity, an extraction section that extracts a dark region in an image corresponding to the image of the object, an information acquisition section that acquires predetermined information different from the extraction result of the dark region by the extraction section and a probability calculation section that calculates a probability value indicating accuracy as a passage target position of the image pickup section using the extraction result of the dark region by the extraction section and the predetermined information.

An endoscope system according to the present invention includes an image pickup section that moves inside an object to be examined and acquires an image of an object in the object to be examined, a position setting section that sets a passage target position of the image pickup section as one pixel position in the dark region of the image corresponding to the image of the object, a state variable calculation section that calculates a state variable indicating a degree of truth and falsehood of the dark region and a probability calculation section that calculates a probability value indicating accuracy of the passage target position based on the state variable.

An endoscope system according to the present invention includes an endoscope provided with an insertion portion inserted into a body cavity of an object to be examined and an image pickup section provided at a distal end portion of the insertion portion to acquire an image of an object in the body cavity, a position setting section that sets a passage target position of the distal end portion as one pixel position in the dark region of the image corresponding to the image of the object, a state variable calculation section that calculates a state variable indicating a degree of truth and falsehood of the dark region and a probability calculation section that calculates a probability value indicating accuracy of the passage target position based on the state variable.

BRIEF DESCRIPTION OF THE DRAWINGS

FIG. 2 is a diagram illustrating an example of processing performed to generate a first probability map;

FIG. 3 is a diagram illustrating an example of an ellipse approximating a dark region;

FIG. 4 is a diagram illustrating an example of processing performed to generate a second probability map;

FIG. 5 is a diagram illustrating an example of processing performed to generate a third probability map;

FIG. 6 is a diagram illustrating correlation between a moving speed v, a rotation speed θ and a bending speed vector;

DETAILED DESCRIPTION OF THE PREFERRED EMBODIMENT(S)

Hereinafter, an embodiment of the present invention will be described with reference to the accompanying drawings.

Figure 1:
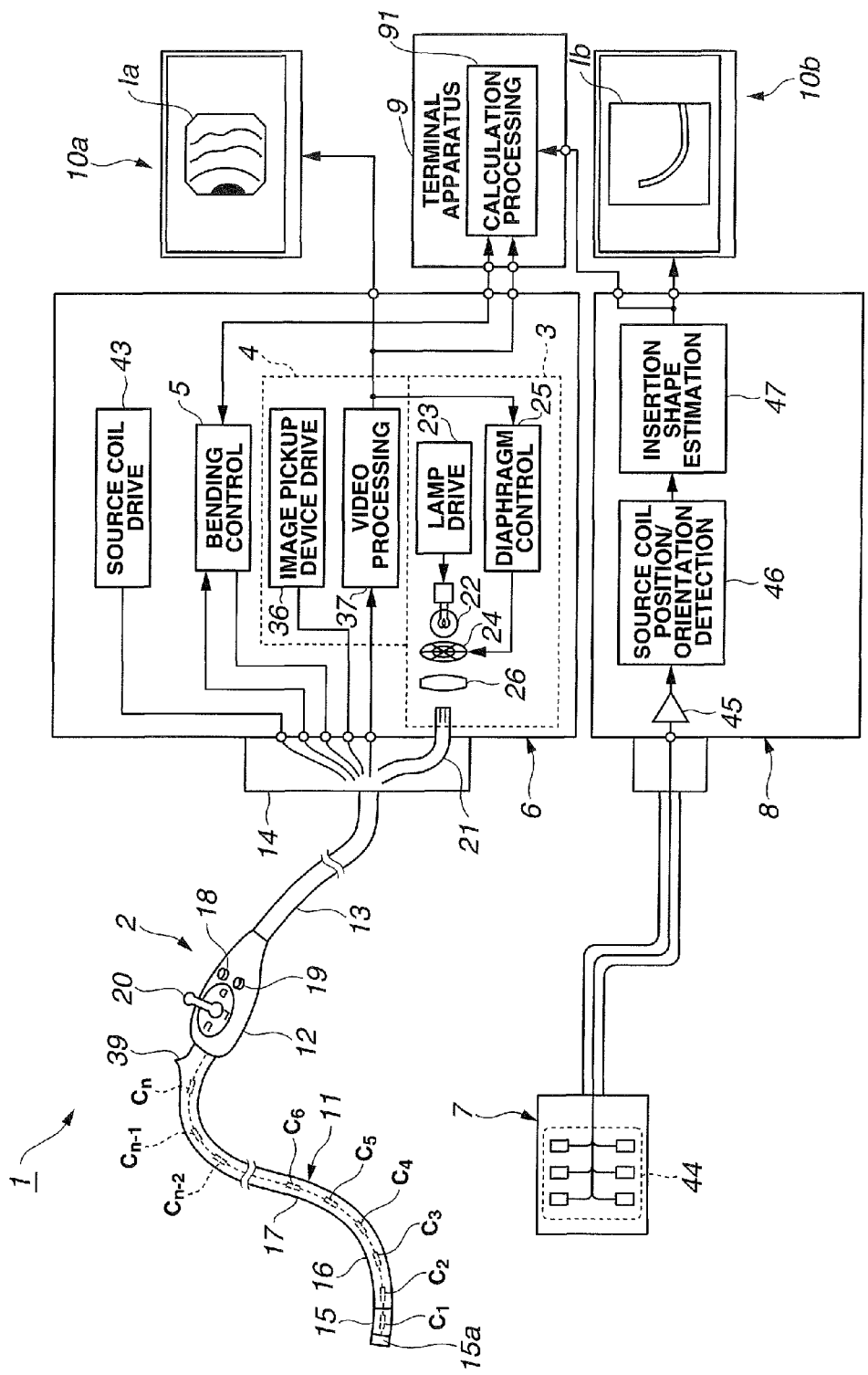
FIG. 1 is a diagram illustrating an example of a configuration of main parts of an endoscope system according to an embodiment of the present invention.
Figure 7:
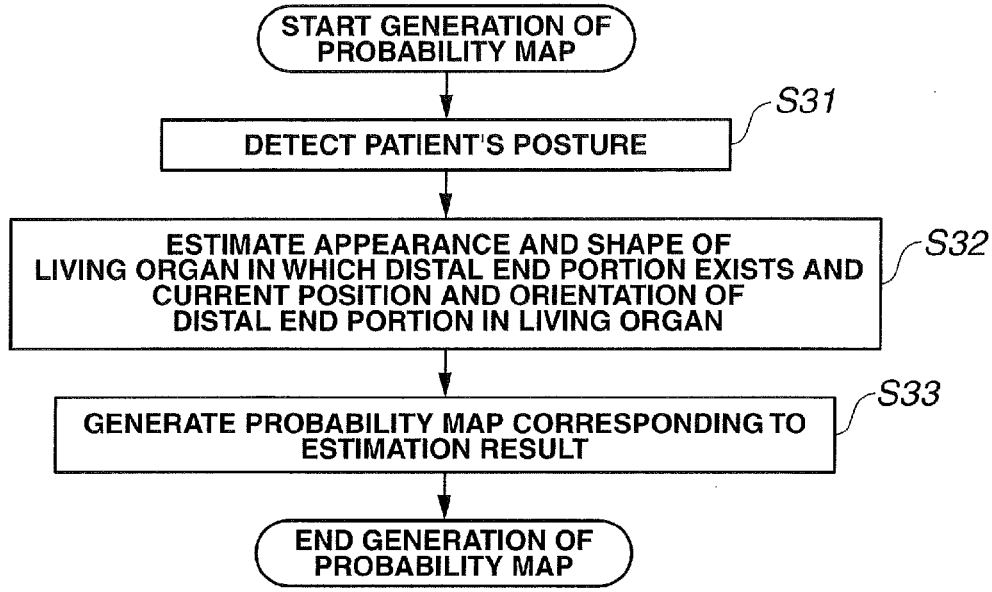
FIG. 7 is a diagram illustrating an example of processing performed to generate a fourth probability map.
Figure 8:
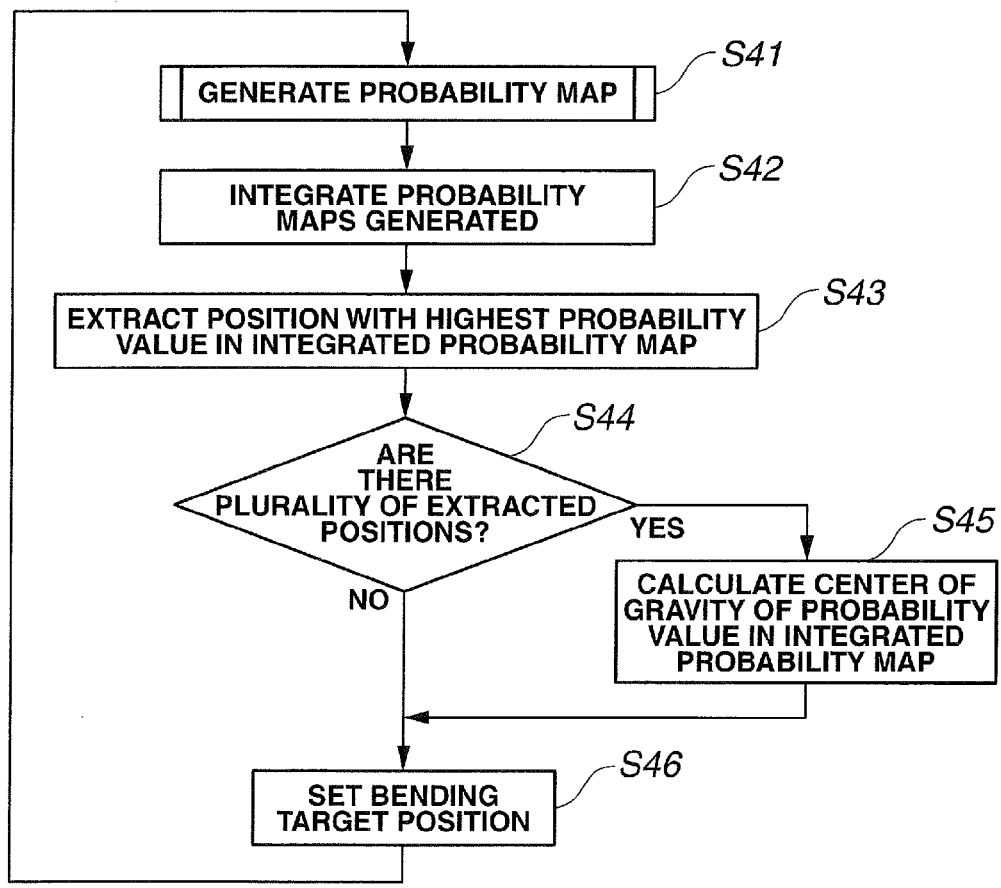
FIG. 8 is a diagram illustrating an example of processing performed to set a bending target position using a probability map.

FIG. 1 to FIG. 19 are related to an embodiment of the present invention. FIG. 1 is a diagram illustrating an example of a configuration of main parts of an endoscope system according to an embodiment of the present invention. FIG. 2 is a diagram illustrating an example of processing performed to generate a first probability map. FIG. 3 is a diagram illustrating an example of an ellipse approximating a dark region. FIG. 4 is a diagram illustrating an example of processing performed to generate a second probability map. FIG. 5 is a diagram illustrating an example of processing performed to generate a third probability map. FIG. 6 is a diagram illustrating correlation between a moving speed v, a rotation speed θ and a bending speed vector. FIG. 7 is a diagram illustrating an example of processing performed to generate a fourth probability map. FIG. 8 is a diagram illustrating an example of processing performed to set a bending target position using a probability map.

Figure 9:
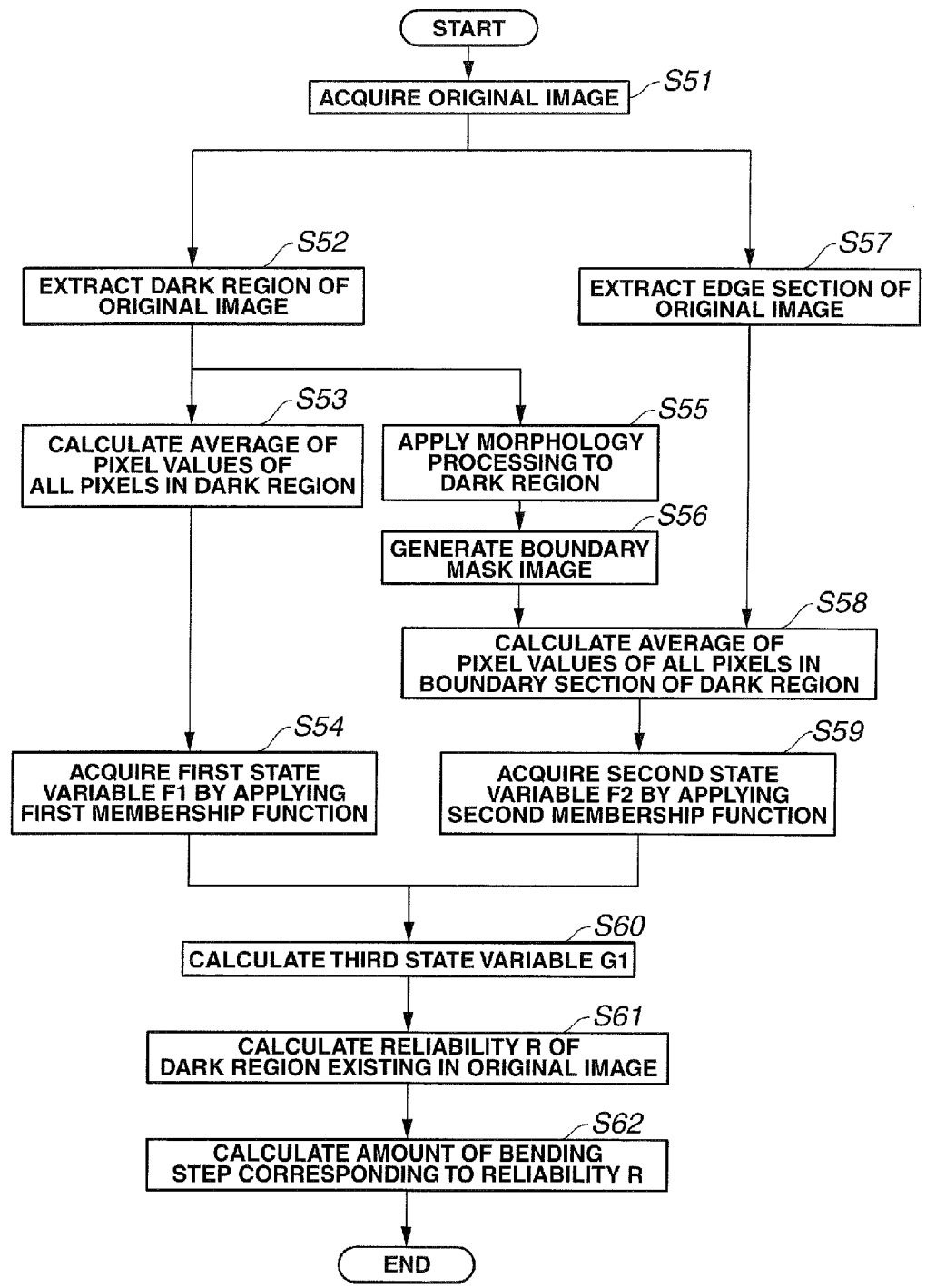
FIG. 9 is a diagram illustrating an example of processing performed to calculate reliability of a dark region existing in an original image.
Figure 10:
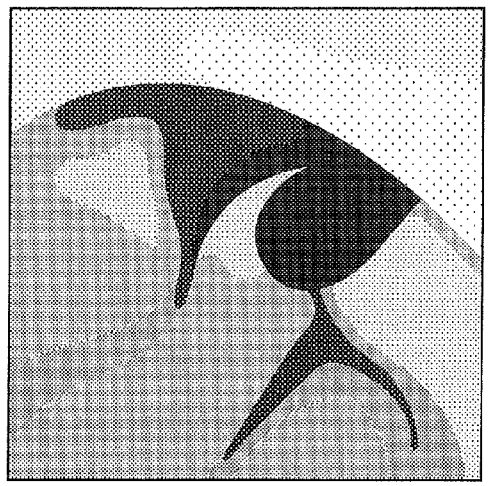
FIG. 10 is a diagram illustrating an example of an original image used for the processing in FIG. 9.
Figure 11:
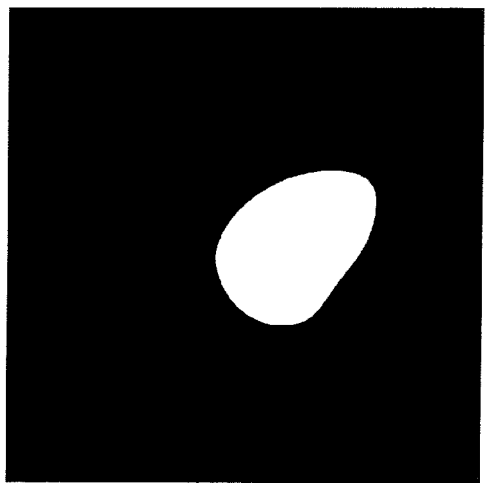
FIG. 11 is a diagram illustrating an example of a dark region mask image generated using the original image in FIG. 10.
Figure 12:
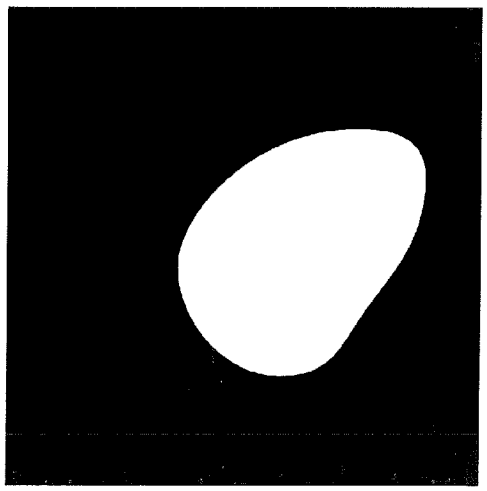
FIG. 12 is a diagram illustrating an example of an expanded image obtained by applying morphology processing to the dark region mask image in FIG. 11.
Figure 13:
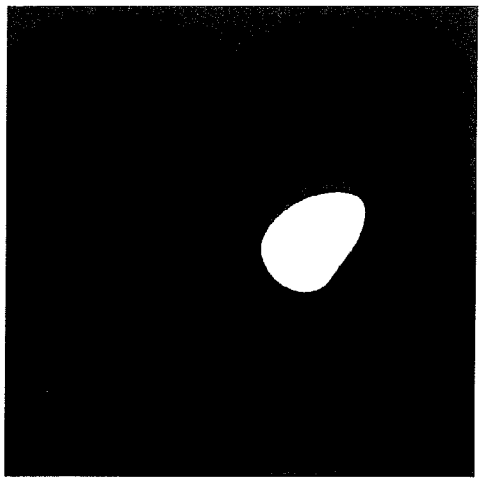
FIG. 13 is a diagram illustrating an example of a contracted image obtained by applying morphology processing to the dark region mask image in FIG. 11.
Figure 14:
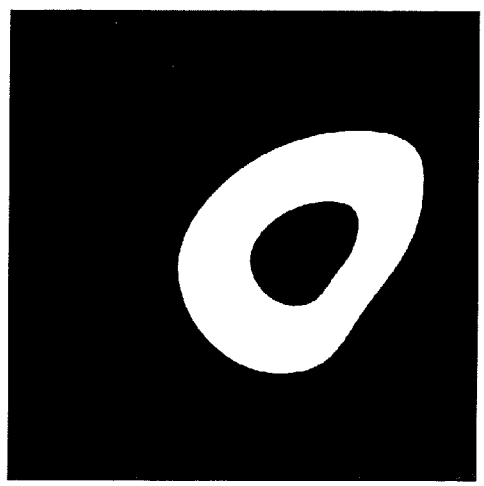
FIG. 14 is a diagram illustrating an example of a boundary mask image generated using the expanded image in FIG. 12 and the contracted image in FIG. 13.
Figure 15:
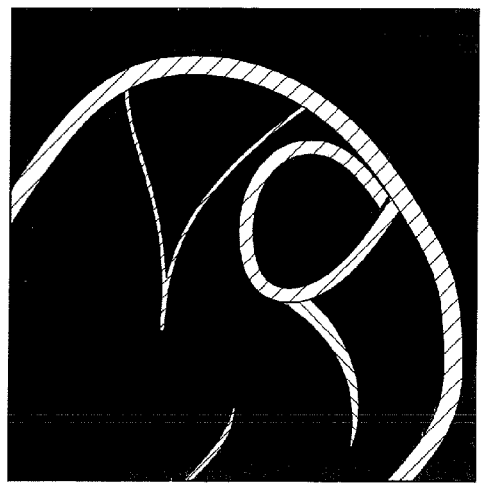
FIG. 15 is a diagram illustrating an example of an edge image generated using the original image in FIG. 10.
Figure 16:
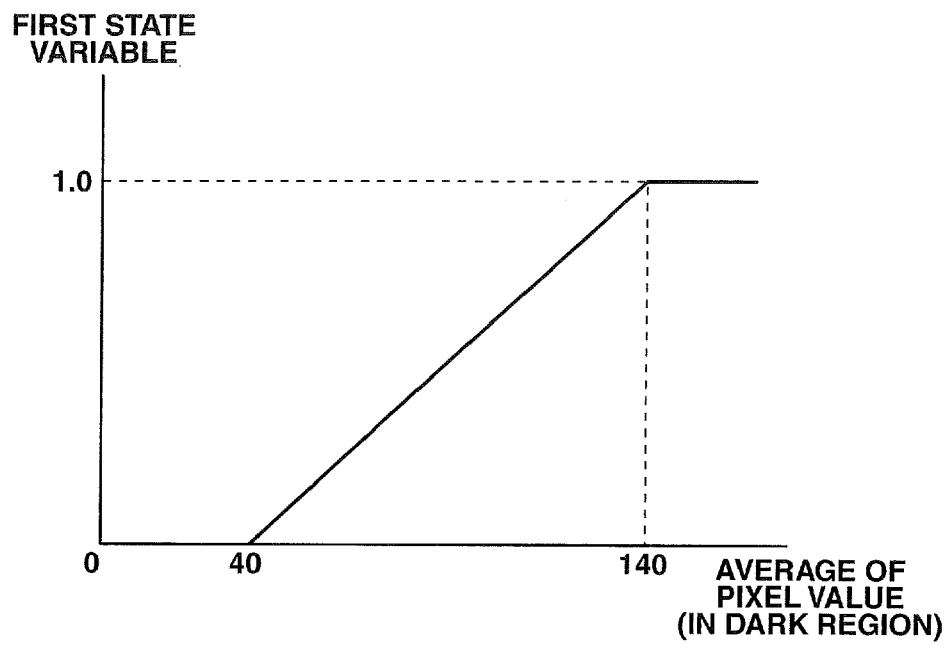
FIG. 16 is a diagram illustrating an example of a first membership function used to acquire a first state variable F1.
Figure 17:
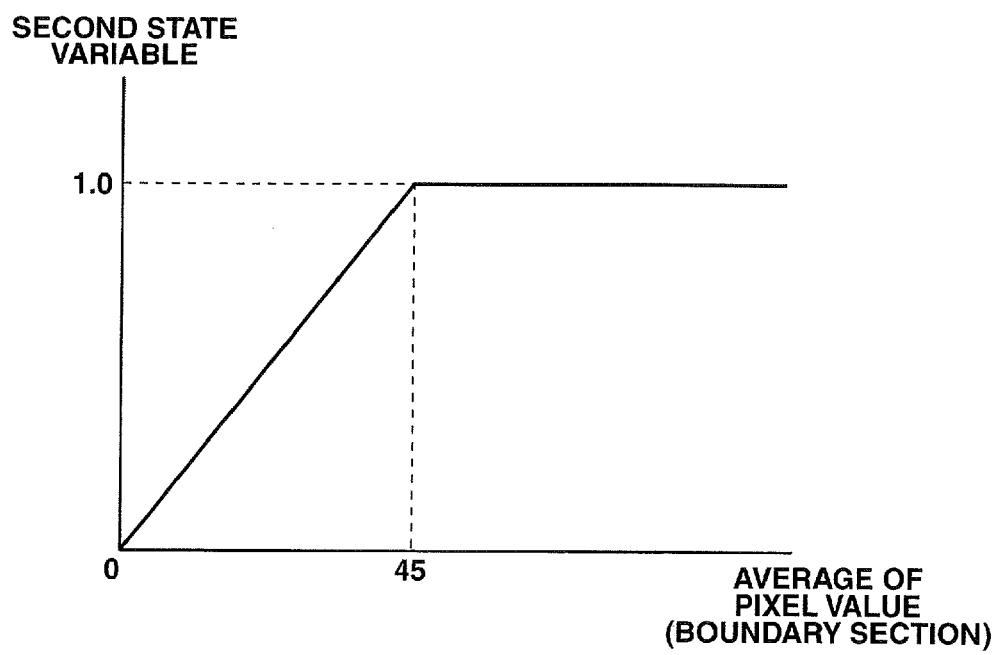
FIG. 17 is a diagram illustrating an example of a second membership function used to acquire a second state variable F2.
Figure 18:
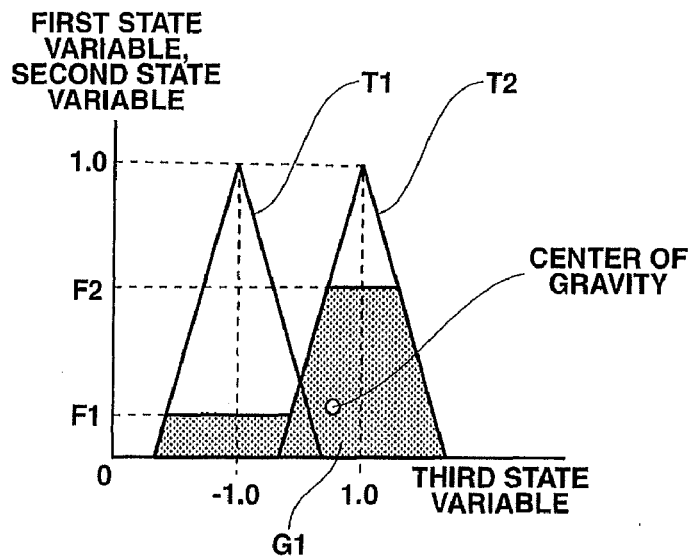
FIG. 18 is a schematic view illustrating how a third state variable G1 is calculated by applying the first state variable F1 and the second state variable F2 to an output fuzzy set.
Figure 19:
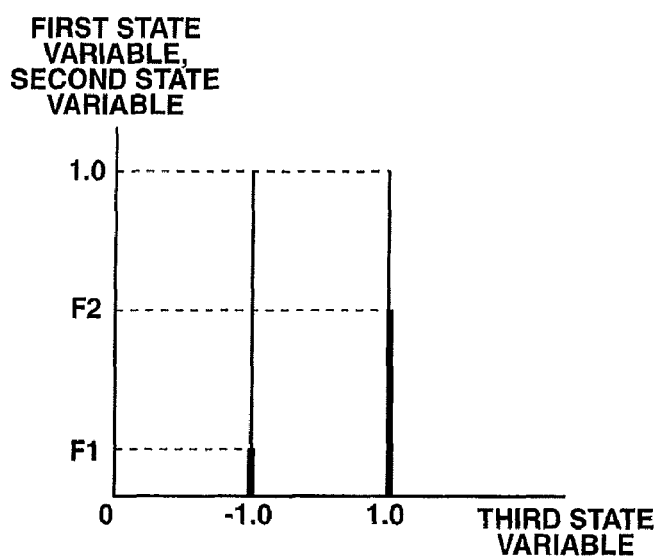
FIG. 19 is a diagram illustrating an example of an output fuzzy set different from that in FIG. 18.

FIG. 9 is a diagram illustrating an example of processing performed to calculate reliability of a dark region existing in an original image. FIG. 10 is a diagram illustrating an example of an original image used for the processing in FIG. 9. FIG. 11 is a diagram illustrating an example of a dark region mask image generated using the original image in FIG. 10. FIG. 12 is a diagram illustrating an example of an expanded image obtained by applying morphology processing to the dark region mask image in FIG. 11. FIG. 13 is a diagram illustrating an example of a contracted image obtained by applying morphology processing to the dark region mask image in FIG. 11. FIG. 14 is a diagram illustrating an example of a boundary mask image generated using the expanded image in FIG. 12 and the contracted image in FIG. 13. FIG. 15 is a diagram illustrating an example of an edge image generated using the original image in FIG. 10. FIG. 16 is a diagram illustrating an example of a first membership function used to acquire a first state variable F1. FIG. 17 is a diagram illustrating an example of a second membership function used to acquire a second state variable F2. FIG. 18 is a schematic view illustrating how a third state variable G1 is calculated by applying the first state variable F1 and the second state variable F2 to an output fuzzy set. FIG. 19 is a diagram illustrating an example of an output fuzzy set different from that in FIG. 18.

As shown in FIG. 1, an endoscope system 1 is configured by including an endoscope 2 inserted into a body cavity of a patient as an object to be examined to pick up an image of the object in the body cavity, a processor 6 to/from which a connector 14 provided in the endoscope 2 can be attached/detached, a sense coil unit 7 disposed in a periphery of a bed on which the patient lies, an endoscope insertion shape detection apparatus 8, a terminal apparatus 9 and monitors 10a and 10b.

Furthermore, the processor 6 includes a light source section 3 that supplies illumination light for illuminating an object which becomes an image pickup target to the endoscope 2, a signal processing section 4 that performs signal processing on an image pickup signal outputted from the endoscope 2 and thereby generates and outputs a video signal, a bending control section 5 that performs bending control on the endoscope 2 and a source coil drive section 43.

The endoscope 2 includes an elongated insertion portion 11 inserted into the body cavity of the object to be examined, an operation section 12 provided at a rear end of the insertion portion 11 and a universal cord 13 that extends out from the operation section 12. The connector 14 attachable/detachable to/from the processor 6 is provided at a rear end of the universal cord 13.

The insertion portion 11 moves in the body cavity of the object to be examined according to an insertion operation by the operator or the like. Furthermore, the insertion portion 11 includes a rigid distal end portion 15 provided at a distal end, a bending portion 16 connected at a rear end of the distal end portion 15 and a flexible tube 17 having flexibility provided between a rear end of the bending portion 16 and a front end of the operation section 12. Furthermore, n source coils C1, C2, . . . , Cn that generate magnetic fields corresponding to a source coil drive signal applied from the source coil drive section 43 are provided at substantially equal intervals inside the insertion portion 11.

An image pickup section 15a provided with an objective optical system that forms an image of an object and an image pickup device that outputs the image of the object formed through the objective optical system as an image pickup signal or the like is provided at the distal end portion 15.

The operation section 12 is provided with a scope switch 18 that instructs acquisition of a freeze image (still image) or the like, a bending mode changeover switch 19 that instructs changeover of the bending mode of the bending portion 16 to a manual mode or an automatic mode and a bending joystick 20 that instructs, when the manual mode is selected, a bending direction and a bending angle of the bending portion 16. Furthermore, a treatment instrument insertion port 39 through which a treatment instrument or the like can be inserted and which leads to a channel (not shown) for the treatment instrument is provided at a portion on the rear end side of the flexible tube 17 and near the front end of the operation section 12.

A light guide 21 that transmits illumination light supplied from the light source section 3 to the distal end portion 15 is inserted into the insertion portion 11 or the like of the endoscope 2.

One end face (incident end face) of the light guide 21 is disposed protruding from the connector 14. On the other hand, the other end face (outgoing end face) of the light guide 21 is disposed in the vicinity of an illumination optical system (not shown) provided at the distal end portion 15. In such a configuration, when the connector 14 is connected to the processor 6, the illumination light supplied from the light source section 3 passes through the light guide 21 and an illumination optical system (not shown) and illuminates the object which is the image pickup target of the image pickup section 15*a*.

The light source section 3 provided with the function as the light source apparatus includes a lamp 22 that emits illumination light which is, for example, white color light, a lamp drive section 23 that supplies power necessary to drive the lamp 22, a diaphragm 24, a diaphragm control section 25 that increases/decreases the amount of diaphragm (amount of aperture) of the diaphragm 24 based on a video signal outputted from the signal processing section 4 and a condensing optical system 26 that supplies the illumination light to the incident end face of the light guide 21 while condensing the illumination light that has passed through the diaphragm 24.

The diaphragm control section 25 calculates average brightness based on, for example, the luminance component of a video signal inputted, increases/decreases the amount of diaphragm (amount of aperture) of the diaphragm 24 based on a difference value which is a value obtained by subtracting a reference value corresponding to appropriate brightness from the average brightness and thereby changes the light quantity of the illumination light that passes through the diaphragm 24 as appropriate.

The signal processing section 4 includes an image pickup device drive section 36 that outputs an image pickup device drive signal to drive an image pickup device provided in the image pickup section 15*a* and a video processing section 37 that generates and outputs a video signal by applying signal processing to the image pickup signal outputted from the image pickup section 15*a*. In this way, the monitor 10*a* displays an endoscope image Ia corresponding to the video signal.

When the bending mode of the bending portion 16 is changed to a manual mode based on an instruction given by the bending mode changeover switch 19, the bending control section 5 performs control to change the direction of bending and the angle of bending of the bending portion 16 based on the direction of inclination and the amount of inclination of the bending joystick 20. Furthermore, when the bending mode of the bending portion 16 is changed to an automatic mode based on an instruction given by the bending mode changeover switch 19, the bending control section 5 provided with the function as a drive control section performs control to change the direction of bending and the angle of bending of the bending portion 16 based on the calculation result of the terminal apparatus 9.

The source coil drive section 43 is connected to the n source coils C1, C2, . . . , Cn provided inside the insertion portion 11 and sequentially applies AC source coil drive signals to the respective source coils. Thus, an AC magnetic field is generated around each source coil provided inside the insertion portion 11.

The sense coil unit 7 is provided with a sense coil group 44 that detects magnetic fields emitted from the n source coils C1, C2, . . . , Cn provided inside the insertion portion 11 and outputs the detected values as magnetic field detection signals.

The endoscope insertion shape detection apparatus 8 includes an amplifier 45 that amplifies the magnetic field detection signals outputted from the sense coil unit 7, a source coil position/orientation detection section 46 that detects three-dimensional coordinate positions and orientations of the n source coils C1, C2, . . . , Cn based on the magnetic field detection signals outputted from the amplifier 45 and outputs the detected values as insertion shape information and an insertion shape estimation section 47 that estimates an insertion shape of the insertion portion 11 based on the insertion shape information outputted from the source coil position/orientation detection section 46 and outputs the estimated value as an insertion shape image signal. In this way, the monitor 10*b* displays an insertion shape image Ib of the insertion portion 11 corresponding to the insertion shape image signal.

The terminal apparatus 9 includes a calculation processing section 91 that carries out a calculation on bending control performed when the bending mode of the bending portion 16 is an automatic mode based on the video signal outputted from the video processing section 37 and the insertion shape image signal outputted from the insertion shape estimation section 47 and outputs the calculation result to the bending control section 5. More specific contents of the calculation performed by the calculation processing section 91 will be described later.

Furthermore, the terminal apparatus 9 is provided with a memory (not shown) that can temporarily store the calculation result or the like of the calculation processing section 91.

Next, operations of the endoscope system 1 will be described. Hereinafter, suppose descriptions of the control when the bending mode changeover switch 19 is changed to the manual bending mode will be omitted and descriptions will be focused on the control when the bending mode changeover switch 19 is changed to the automatic bending mode.

The operator connects and starts each section of the endoscope system 1 first, and then inserts the insertion portion 11 of the endoscope 2 into the body cavity of the patient and changes the bending mode changeover switch 19 to the automatic bending mode. Accordingly, image pickup of the object by the image pickup section 15*a* of the endoscope 2 starts and each source coil provided in the insertion portion 11 starts to generate a magnetic field.

An image pickup signal outputted from the image pickup section 15*a* along with image pickup of the object is outputted to the processor 6 through the universal cord 13 and the connector 14, converted to a video signal by the video processing section 37 and then inputted to the calculation processing section 91 of the terminal apparatus 9. On the other hand, a magnetic field detection signal outputted from the sense coil unit 7 along with generation of the magnetic field in each source coil provided in the insertion portion 11 is amplified by the amplifier 45, converted as three-dimensional coordinate information of the source coil by the source coil position/orientation detection section 46, an insertion shape thereof is estimated by the insertion shape estimation section 47, and then inputted to the calculation processing section 91 of the terminal apparatus 9 as an insertion shape image signal.

The calculation processing section 91 of the terminal apparatus 9 performs processing based on the inputted video signal and insertion shape image signal or the like, thereby sets a bending target position (passage target position) which becomes a passage target of the distal end portion 15 and outputs information on the set bending target position to the bending control section 5.

Here, the processing performed by the calculation processing section 91 when setting the aforementioned bending target position will be described.

The calculation processing section 91 provided with the function as an extraction section calculates the dark region of an image (endoscope image) corresponding to the video signal inputted and the center of gravity of the dark region (step S1 in FIG. 2).

The center of gravity of the dark region calculated in step S1 in FIG. 2 matches the center of moment of pixel values of the dark region, that is, the center of gravity of the dark region is calculated as a pixel position of ($\mu 10/\mu 00$, $\mu 01/\mu 00$) using Equation (1) below as the technique of calculating a moment of a digital image.

$$\mu_{mn} = \sum_x \sum_y x^m y^n f(x, y) \quad (1)$$

After that, the calculation processing section 91 calculates an ellipse whose center is the center of gravity ($\mu 10/\mu 00$, $\mu 01/\mu 00$) of the dark region calculated in step S1 in FIG. 2 based on second moments $\mu 20$, $\mu 11$ and $\mu 02$ of the pixel values of the dark region and 0th moment $\mu 00$ of the pixel value of the dark region (step S2 in FIG. 2).

To be more specific, with regard to the calculation result of the dark region, for example, shown in FIG. 3, the calculation processing section 91 calculates an ellipse approximating the dark region having center coordinates ($\mu 10/\mu 00$, $\mu 01/\mu 00$), length of the major axis a, length of the minor axis b and inclination $\phi$ of the major axis with respect to the horizontal direction of the image based on the second moments $\mu 20$, $\mu 11$ and $\mu 02$ of pixel values of the dark region and the 0th moment $\mu 00$ of a pixel value of the dark region. The length of the major axis a, length of the minor axis b and inclination $\phi$ of the major axis with respect to the horizontal direction of the image are expressed using following Equations (2) to (4) respectively.

$$a^2 = \frac{2\{\mu_{20} + \mu_{02} + \sqrt{4\mu_{11}^2 + (\mu_{20} - \mu_{02})^2}\}}{\mu_{00}} \quad (2)$$

$$b^2 = \frac{2\{\mu_{20} + \mu_{02} - \sqrt{4\mu_{11}^2 + (\mu_{20} - \mu_{02})^2}\}}{\mu_{00}} \quad (3)$$

$$\phi = \frac{1}{2}\tan^{-1}\frac{2\mu_{11}}{\mu_{20} - \mu_{02}} \quad (4)$$

The calculation processing section 91 then projects a two-dimensional normal distribution in the ellipse calculated in step S2 in FIG. 2 onto a probability map (step S3 in FIG. 2).

That is, the calculation processing section 91 performs the processing in step S1 to step S3 in FIG. 2 and thereby generates a first probability map corresponding to the pixel values of the endoscope image obtained by the endoscope 2.

Suppose each probability map generated in the present embodiment is formed with one probability value assigned to one pixel of the endoscope image.

Furthermore, the aforementioned first probability map is not limited to that generated through the processing in step S1 to step S3 in FIG. 2, but may also be generated by applying a predetermined function to each pixel value of the endoscope image, for example, such that the probability value of a bright region becomes relatively low and the probability value of a dark region becomes relatively high. To be more specific, when, for example, the probability value corresponding to a pixel value C(x, y) of the original image is assumed to be P(x, y), the aforementioned first probability map may be generated using Equation (5) below.

$$P(x, y) = (255 - C(x, y))/255 \quad (5)$$

Suppose the pixel value C(x, y) in Equation (5) above takes a value of 0 or more and 255 or less.

On the other hand, the calculation processing section 91 having the function as an information acquisition section detects the current posture of the patient based on a predetermined input signal in which at least information on the dorsoventral direction of the patient is included (step S11 in FIG. 4).

The predetermined input signal may also be a signal outputted according to the detection result of the position and orientation of a coil (not shown) attached to the patient or may be a signal outputted according to the instruction contents in a posture selection switch provided in the scope switch 18 or the like.

After that, the calculation processing section 91 identifies the dorsoventral direction (dorsal side and ventral side) in the image (endoscope image) corresponding to the inputted video signal based on the detection result in step S11 in FIG. 4 and the insertion shape image signal (step S12 in FIG. 4).

However, when a general insertion operation of the endoscope is considered, it is possible to assume that bending the distal end portion of the endoscope toward the ventral side or dorsal side of the patient is relatively rare. The calculation processing section 91 then generates a probability map in which the probabilities of regions corresponding to the dorsal side and ventral side of the endoscope image are set to be relatively low based on a first algorithm constructed based on such an assumption and the identification result in step S12 in FIG. 4 (step S13 in FIG. 4).

That is, the calculation processing section 91 generates a second probability map corresponding to the current posture of the patient, in whom the endoscope 2 is inserted by performing the processing in step S11 to step S13 in FIG. 4.

On the other hand, the calculation processing section 91 having the function as an information acquisition section calculates a bending speed vector corresponding to the moving speed of the distal end portion 15 (image pickup section 15a) by reading, for example, control contents of the bending control section 5 (step S21 in FIG. 5).

To be more specific, the calculation processing section 91 calculates a bending speed vector based on the control contents of the bending control section 5 assuming the center of the endoscope image as a starting point on the image plane of the endoscope image, the moving speed indicating the amount of movement of the distal end portion 15 in one frame as v and further the rotation speed indicating the amount of rotation of the distal end portion 15 in one frame on the image plane of the endoscope image as $\theta$. The moving speed v, rotation speed $\theta$ and bending speed vector here are, for example, as shown in FIG. 6 in the endoscope image in the current frame.

After that, the calculation processing section 91 estimates the direction the distal end portion 15 is directed next as a direction from the starting point (center of the endoscope image) to the end point of the bending speed vector based on the calculation result of the bending speed vector obtained in step S21 in FIG. 5 (step S22 in FIG. 5).

However, when a general bending operation of the endoscope is considered, it is possible to assume that there is a high possibility that the bending target position may exist at the image position in the case where the direction and speed in which the bending portion is actually driven to bend continue, that is, the end point of the aforementioned bending speed vector.

The calculation processing section 91 then projects an ellipsoidal two-dimensional normal distribution centered on the end point (v, θ) of the bending speed vector of the endoscope image in the current frame onto the probability map based on a second algorithm constructed in accordance with such an assumption and the estimation result in step S22 in FIG. 5 (step S23 in FIG. 5).

That is, the calculation processing section 91 performs the processing in step S21 to step S23 in FIG. 5 and thereby generates a third probability map corresponding to the bending speed of the endoscope 2 inserted in the body cavity of the patient.

On the other hand, the calculation processing section 91 performs processing similar to the processing described as step S11 in FIG. 4 and thereby detects the current posture of the patient (step S31 in FIG. 7).

After that, the calculation processing section 91 estimates the appearance and shape of the living organ in which the distal end portion 15 exists and the current position and orientation of the distal end portion 15 in the living organ based on the detection result in step S31 in FIG. 7 and an insertion shape image signal (step S32 in FIG. 7).

The calculation processing section 91 then generates a probability map corresponding to the estimation result in step S32 in FIG. 7 (step S33 in FIG. 7). To be more specific, when the calculation processing section 91 obtains, for example, an estimation result that the distal end portion 15 is currently located in the descending colon and that the distal end portion 15 is oriented toward the head of the patient, the calculation processing section 91 generates a probability map in which probabilities of the regions corresponding to the front and quasi-front of the distal end portion 15 are set to be relatively high.

That is, the calculation processing section 91 performs the processing in step S31 to step S33 in FIG. 7 and thereby generates a fourth probability map corresponding to the current position and orientation of the distal end portion 15.

On the other hand, based on one bending target position set in the past (e.g., bending target position set the last time), the calculation processing section 91 projects a two-dimensional normal distribution centered on the one bending target position and thereby generates a fifth probability map.

The calculation processing section 91 then performs processing of generating the aforementioned first to fifth probability maps as processing shown in step S41 in FIG. 8.

Next, the calculation processing section 91 performs processing for integrating the respective probability maps generated in the processing in step S41 in FIG. 8 (step S42 in FIG. 8).

To be more specific, the calculation processing section 91 calculates an integrated value Cx at the one position according to following Equation (6), where the probability value of one position (pixel position) in the first probability map is P1, the probability value of the one position in the second probability map is P2, the probability value of the one position in the third probability map is P3, the probability value of the one position in the fourth probability map is P4 and the probability value of the one position in the fifth probability map is P5.

$$Cx = \mu a \times P1 + \mu b \times P2 + \mu c \times P3 + \mu d \times P4 + \mu e \times P5 \qquad (6)$$

In Equation (6) above, suppose μa denotes a weight value assigned to the first probability map, μb denotes a weight value assigned to the second probability map, denotes a weight value assigned to the third probability map, μd denotes a weight value assigned to the fourth probability map and μe denotes a weight value assigned to the fifth probability map.

Furthermore, the aforementioned integrated value Cx is not limited to that calculated by the weighting calculation as shown in Equation (6) above, but may also be calculated using other calculation techniques such as fuzzy logic calculation or mixture of experts model.

After that, the calculation processing section 91 performs processing of calculating the integrated value Cx on all positions (pixel positions) within one screen using Equation (6) above, and then applies normalization processing so that each calculated integrated value Cx becomes a value of 0 or more and 1 or less.

When the above described processing is performed as the processing in step S42 in FIG. 8, a new one probability map is generated in which five probability maps of the first to fifth probability maps are integrated.

That is, the integrated value Cx after the aforementioned normalization processing is applied corresponds to a probability value indicating the accuracy as the bending target position (passage target position of distal end portion 15 or image pickup section 15a).

The calculation processing section 91 extracts a position (pixel position) with the highest probability value in the integrated probability map generated by the processing in step S42 in FIG. 8 (step S43 in FIG. 8) and then judges whether or not there are a plurality of positions (pixel positions) (step S44 in FIG. 8).

When there are a plurality of positions extracted by the processing in step S43 in FIG. 8, the calculation processing section 91 calculates the center of gravity (center of moment) of the probability value in the integrated probability map (step S45 in FIG. 8) and sets the position (pixel position) corresponding to the center of gravity as the bending target position (step S46 in FIG. 8).

Furthermore, when there is only one position extracted by the processing in step S43 in FIG. 8, the calculation processing section 91 sets the position (pixel position) as the bending target position (step S46 in FIG. 8).

The calculation processing section 91 then outputs information on the bending target position set by the processing in step S46 in FIG. 8 to the bending control section 5 and then repeats a series of processes from step S41 in FIG. 8 over again.

As described above, the endoscope system 1 of the present embodiment performs a series of processes regarding FIG. 2 to FIG. 8 in an automatic bending mode, and can thereby accurately calculate a target position to which the distal end portion of the endoscope is directed. As a result, the endoscope system 1 of the present embodiment can insert the endoscope more smoothly than conventional ones.

According to the series of processes shown in FIG. 2 to FIG. 8, an integrated probability map need not always be created using all the first to fifth probability maps, but an integrated probability map may also be created using, for example, only the first and second probability maps.

Furthermore, the fifth probability map generated in the series of processes shown in FIG. 2 to FIG. 8 is not always generated based on the one bending target position set in the past, but, for example, the integrated probability map created the last time may also be used as is.

On the other hand, according to the endoscope system 1 of the present embodiment, a series of processes regarding FIG. 9 to FIG. 19 may be performed in an automatic bending mode so that the endoscope can be inserted smoothly.

First, the calculation processing section 91 acquires an original image corresponding to an inputted video signal, for example, as shown in FIG. 10 (step S51 in FIG. 9).

After that, the calculation processing section 91 extracts a dark region that exists in the original image obtained in step S51 in FIG. 9 (step S52 in FIG. 9). To be more specific, the calculation processing section 91 extracts an isolated region having a pixel value less than a predetermined value out of the original image obtained in step S51 in FIG. 9 as the dark region. By performing such processing, the calculation processing section 91 generates a dark region mask image as shown in FIG. 11 from the original image shown in FIG. 10 by uniformly setting pixel values of the dark region to 255 and uniformly setting pixel values of the non-dark region to 0.

The calculation processing section 91 calculates an average of pixel values of all pixels in the dark region while regarding pixels existing in the region masked by the dark region mask image shown in FIG. 11 out of the original image shown in FIG. 10 as pixels in the dark region (step S53 in FIG. 9).

After that, the calculation processing section 91 applies the average of pixel values of all pixels existing in the dark region calculated by the processing in step S53 in FIG. 9 to a first membership function shown in FIG. 16 and thereby acquires a first state variable F1 to be used for a fuzzy logic calculation (step S54 in FIG. 9).

The aforementioned first membership function is a function that expresses the degree of darkness of the dark region extracted through the processing in step S52 and step S53 in FIG. 9 with a value $0 \leq F1 \leq 1$, which is set to take a value closer to F1=0 when the dark region is darker or take a value closer to F1=1 when the dark region is brighter. To be more specific, as shown in FIG. 16, the first membership function according to the present embodiment is set to become F1=0 when the average of pixel values of all pixels in the dark region is 40 or less, F1=1 when the average is 140 or more and linearly increase within 0<F1<1 when the average is more than 40 and less than 140.

Furthermore, the calculation processing section 91 applies morphology processing to the dark region mask image generated in step S52 in FIG. 9 (step S55 in FIG. 9). The calculation processing section 91 then performs processing in step S55 in FIG. 9 and thereby acquires an expanded image obtained by expanding the dark region extracted in step S52 in FIG. 9 (region of pixel value=255) and a contracted image obtained by contracting the dark region. The expanded image and contracted image obtained by performing the processing in step S55 in FIG. 9 are as shown, for example, in FIG. 12 and FIG. 13.

The calculation processing section 91 generates a boundary mask image using the expanded image and contracted image obtained through the processing in step S55 in FIG. 9 (step S56 in FIG. 9). To be more specific, the calculation processing section 91 generates a boundary mask image as shown, for example, in FIG. 14 by setting to 0 pixel values in a region that overlaps with the dark region (region of pixel value=255) of the contracted image out of the dark region (region of pixel value=255) of the expanded image.

On the other hand, the calculation processing section 91 extracts an edge section existing in the original image obtained in step S51 in FIG. 9 (step S57 in FIG. 9) and thereby acquires an edge image. To be more specific, the calculation processing section 91 applies a Laplacian filter to the original image obtained in step S51 in FIG. 9 and thereby acquires an edge image as shown, for example, in FIG. 15 with the edge section extracted from the original image.

The calculation processing section 91 calculates an average of pixel values of all pixels in the boundary section while regarding pixels existing in the region masked by the boundary mask image obtained in step S56 in FIG. 9 out of the edge images obtained in step S57 in FIG. 9 as pixels existing in the boundary section of the dark region (step S58 in FIG. 9).

After that, the calculation processing section 91 applies the average of pixel values of all pixels existing in the boundary section of the dark region calculated through the processing in step S58 in FIG. 9 to a second membership function shown in FIG. 17 and thereby acquires a second state variable F2 used for a fuzzy logic calculation (step S59 in FIG. 9).

The aforementioned second membership function is a function that expresses the degree of brightness of the boundary section (of the dark region) extracted through the processing in step S55 to step S58 in FIG. 9 with a value which is set to take a value closer to F2=0 when the boundary section is blur or take a value closer to F2=1 when the boundary section is clear. To be more specific, as shown in FIG. 17, the second membership function according to the present embodiment is set to become F2=0 when the average of pixel values of all pixels of the edge images in the boundary section of the dark region is 0, F2=1 when the average is 45 or more and linearly increase within 0<F2<1 when the average is more than 0 and less than 45.

The calculation processing section 91 calculates a third state variable G1 as a value expressing a degree of truth and falsehood of the dark region using an output fuzzy set created according to a predetermined rule, the first state variable F1 obtained in step S54 in FIG. 9 and the second state variable F2 obtained in step S59 in FIG. 9 (step S60 in FIG. 9).

According to the present embodiment, the aforementioned predetermined rule is defined as a logic equation based on a fuzzy logic of "IF(*F1 and F2) THEN dark region" when, for example, the logical negation of the first state variable F1 is expressed as *F1.

Furthermore, the aforementioned predetermined rule defines G1=1 in the case where the pixel value inside the dark region is small (not large) and the boundary section of the dark region is clear, that is, a true dark region.

Furthermore, the aforementioned predetermined rule defines G1=1 in the case where the pixel value inside the dark region is large and the boundary section of the dark region is blur, that is, a false dark region.

The output fuzzy set created using each element defined as described above is as shown, for example, in FIG. 18 with triangles corresponding to the first state variable F1 and second state variable F2 respectively arranged on coordinate axes with the values of the first state variable F1 and second state variable F2 assigned to the vertical axis and the value of the third state variable G1 assigned to the horizontal axis.

The triangle corresponding to the first state variable F1 is a set indicating a false dark region, and formed as an isosceles triangle T1 as shown in FIG. 18, the vertex of which is arranged at a coordinate position where F1=1 and G1=1 and the base of which is arranged at F1=0. On the other hand, the triangle corresponding to the second state variable F2 is a set indicating a true dark region, and formed as an isosceles triangle T2 as shown in FIG. 18, whose vertex is arranged at a coordinate position where F2=1 and G1=1 and the base of which is arranged at F2=0.

Here, an overview of processing performed to calculate the third state variable G1 will be described using FIG. 18.

The calculation processing section 91 applies the value of the first state variable F1 obtained in step S54 in FIG. 9 to the output fuzzy set illustrated in FIG. 18. When such processing is visually expressed, the processing corresponds to the interior of the isosceles triangle T1 in FIG. 18 being painted up to the height (value of the vertical axis) corresponding to the value of the first state variable F1.

Furthermore, the calculation processing section 91 applies the value of the second state variable F2 obtained in step S59 in FIG. 9 to the output fuzzy set illustrated in FIG. 18. When such processing is visually expressed, the processing corresponds to the interior of the isosceles triangle T2 being painted up to the height (value of the vertical axis) corresponding to the value of the second state variable F2.

The calculation processing section 91 calculates the center of gravity of the graphics made up of the entire painted area of the isosceles triangles T1 and T2 in FIG. 18 and calculates the value of the coordinate position of the center of gravity on the horizontal axis as the third state variable G1.

According to the above described processing, the output characteristic of the third state variable G1 can be said to depend on the lengths of the bases of the isosceles triangles T1 and T2. Thus, by applying the first state variable F1 and the second state variable F2 to the output fuzzy set in FIG. 19 assuming, for example, that the lengths of the bases of the isosceles triangles T1 and T2 are substantially 0, it is possible to obtain a calculation result different from that in the case where the output fuzzy set in FIG. 18 is used.

The third state variable G1 when the first state variable F1 and the second state variable F2 are applied to the output fuzzy set in FIG. 19 can be obtained by Equation (7) below.

$$G1 = \frac{\sum_{i=1}^{2} F_i x_i}{\sum_{i=1}^{2} F_i} \quad (7)$$

Here, suppose x1=−1 and x2=1 in Equation (7) above. After that, the calculation processing section 91 normalizes the third state variable G1 calculated in step S60 in FIG. 9 using Equation (8) below and thereby calculates reliability R as a value stochastically expressing whether or not the dark region existing in the original image is accurate as the direction toward which the distal end portion 15 is directed (step S61 in FIG. 9).

$$R=(G1+1)/2 \quad (8)$$

On the other hand, the calculation processing section 91 applies a series of processes regarding FIG. 2 to FIG. 8 or publicly known processing to the original image acquired in step S51 in FIG. 9 and thereby calculates the bending target position (passage target position of the distal end portion 15) of the bending portion 16 as one pixel position in the dark region of the original image.

Here, assuming that the distance from the center of the original image to the bending target position is d and the coefficient for converting the distance in the image to an actual distance is k, the amount of bending step Sa expressing the amount of bending of the bending portion 16 (insertion portion 11) per unit time is calculated using, for example, Equation (9) below.

$$Sa=F(d)=k \times d \quad (9)$$

On the other hand, the calculation processing section 91 applies a linear conversion using Equation (10) below to the amount of bending per unit time of the bending portion 16 and thereby calculates the amount of bending step Sb corresponding to reliability R (step S62 in FIG. 9).

$$Sb=G(d, R)=(k \times d) \times R \quad (10)$$

The calculation processing section 91 need not always apply a linear conversion to the amount of bending per unit time of the bending portion 16 to calculate the amount of bending step Sb. To be more specific, as long as the calculation processing section 91 performs a calculation such that the value of the amount of bending step Sb increases as the value of reliability R increases and the value of the amount of bending step Sb decreases as the value of reliability R decreases, the calculation processing section 91 may also calculate the amount of bending step Sb by applying a non-linear conversion to the amount of bending per unit time of the bending portion 16.

After that, the calculation processing section 91 outputs the calculated amount of bending step Sb to the bending control section 5. This causes the bending portion 16 to bend according to the amount of bending step Sb calculated every time the original image is acquired.

As described above, the endoscope system 1 of the present embodiment performs a series of processes regarding FIG. 9 to FIG. 19 in an automatic bending mode, and can thereby set the amount of bending per unit time of the bending portion 16 according to a degree of truth and falsehood of the dark region existing in the original image.

Therefore, when noise is mixed into the acquired original image and a target position is obtained which cannot be considered appropriate as the direction toward which the distal end portion of the endoscope is directed, the endoscope system 1 of the present embodiment can suppress the bending operation to the target position by reducing the amount of bending per unit time. On the other hand, when a target position is obtained which is considered appropriate as the direction toward which the distal end portion of the endoscope is directed, the endoscope system 1 of the present embodiment can quickly perform the bending operation to the target position.

The value of the aforementioned reliability R is not limited to the one calculated using the fuzzy logic calculation shown as a series of processes regarding FIG. 9 to FIG. 19 but may also be calculated using other calculation techniques such as a mixture of experts model.

Furthermore, a series of processes regarding FIG. 9 to FIG. 19 is not always used in the case where after reliability of one dark region extracted from the original image is calculated, the amount of bending per unit time of the bending portion 16 is set as that corresponding to the reliability. To be more specific, the processing regarding FIG. 9 to FIG. 19 can also be applied for such control that after reliability of two or more dark regions extracted from the original image is calculated, the bending portion 16 is bent so that the distal end portion 15 is directed to one dark region having relatively highest reliability.

On the other hand, according to the present embodiment, it is possible to generate a more accurate integrated probability map by using the reliability R calculated in the series of processes shown in FIG. 9 to FIG. 19 to correct the first probability map generated in the series of processes shown in FIG. 2 to FIG. 8. To be more specific, it is possible to use a method of correcting the first probability map by calculating a probability value Pc (x, y) using Equation (11) below which multiplies the probability value P(x, y) shown in Equation (5) above by the reliability R.

$$Pc(x, y) = P(x, y) \times R \qquad (11)$$
$$= \{(255 - C(x, y))/255\} \times R$$

By correcting the first probability map using Equation (11) above, the contribution of the first probability map in the integrated probability map is appropriately adjusted as that corresponding to the reliability R, and it is thereby possible to generate a more accurate integrated probability map.

Furthermore, the above described processing is not limited to that used together with the setting of a bending target position of the endoscope provided with a bendable insertion portion, but may also be used together with the setting of the destination of a capsule endoscope that moves according to peristaltic movement of a living body.

The present invention is not limited to the aforementioned embodiment, but it goes without saying that the present invention can be modified or applied in various ways without departing from the spirit and scope of the invention.

What is claimed is:

1. An endoscope system comprising:
    an image pickup section that picks up an image of an object inside a subject to be examined;
    a position detection section that detects a position of a predetermined object in the image of the object obtained by the image pickup section;
    a probability calculation section that calculates a plurality of kinds of probability values which are different from one another, at least based on a result of extraction of a dark region in the image picked up by the image pickup section and a result of calculation of a moving speed of the image pickup section; and
    a calculation section that obtains a value indicating accuracy of the position of the predetermined object detected by the position detection section by performing calculation for integrating the plurality of kinds of probability values calculated by the probability calculation section.

2. The endoscope system according to claim 1, wherein the probability calculation section calculates a plurality of kinds of probability values which are different from one another based on the result of extraction of the dark region in the image picked up by the image pickup section the result of calculation of the moving speed of the image pickup section, and a result of detection of posture of the object to be examined.

3. The endoscope system according to claim 1, wherein the position detection section corrects the position of the predetermined object based on the value obtained as a result of the calculation by the calculation section.

4. The endoscope system according to claim 1, wherein the position of the predetermined object is a passage target position of the image pickup section.

5. An endoscope system comprising:
    an endoscope provided with an insertion portion inserted into a body cavity of a subject to be examined and an image pickup section provided at a distal end portion of the insertion portion;
    a position setting section that sets a target position through which the distal end portion is made to pass in the image of an object obtained by the image pickup section;
    a probability calculation section that calculates a plurality of kinds of probability values which are different from one another, at least based on a result of extraction of a dark region in the image picked up by the image pickup section, a result of calculation of a moving speed of the image pickup section, and a result of a detection of a position and an orientation of the distal end portion in the body cavity; and
    a calculation section that obtains a value indicating accuracy of the target position set by the position setting section by performing calculation for integrating the plurality of kinds of probability values calculated by the probability calculation section.

6. The endoscope system according to claim 5, wherein the probability calculation section calculates a plurality of kinds of probability values which are different from one another, based on the result of extraction of the dark region in the image picked up by the image pickup section, the result of calculation of the moving speed of the image pickup section, the result of detection of the position and the orientation of the distal end portion in the body cavity, and a result of detection of posture of an object to be examined.

7. The endoscope system according to claim 5, wherein the position setting section corrects the target position based on the value obtained as a result of the calculation by the calculation section.

8. The endoscope system according to claim 5, further comprising a drive control section that drives and controls the endoscope based on the value obtained as a result of the calculation by the calculation section.

9. The endoscope system according to claim 5, wherein the position setting section sets, among pixels of the image, a pixel position at which the value obtained as a result of the calculation by the calculation section is the highest, as the target position.

10. An endoscope system comprising:
    an image pickup section that moves inside an object to be examined and acquires an image of an object in the object to be examined;
    a position setting section that sets a passage target position of the image pickup section as one pixel position in a dark region of the image corresponding to the image of the object;
    a state variable calculation section that calculates a first state variable by applying an average of pixel values in the dark region to a first membership function, calculates a second state variable by applying an average of pixel values of an edge image in a boundary section of the dark region to a second membership function, and further calculates a third state variable indicating a degree of truth and falsehood of the dark region, based on a result obtained by applying the first state variable and the second state variable to a fuzzy set created according to a predetermined rule; and
    a probability calculation section that calculates a probability value indicating accuracy of the passage target position based on the state variable.

11. An endoscope system comprising:
    an endoscope provided with an insertion portion inserted into a body cavity of an object to be examined and an image pickup section provided at a distal end portion of the insertion portion to acquire an image of an object in the body cavity;
    a position setting section that sets a passage target position of the distal end portion as one pixel position in a dark region of the image corresponding to the image of the object;

a state variable calculation section that calculates a first state variable by applying an average of pixel values in the dark region to a first membership function, calculates a second state variable by applying an average of pixel values of an edge image in a boundary section of the dark region to a second membership function, and further calculates a third state variable indicating a degree of truth and falsehood of the dark region, based on a result obtained by applying the first state variable and the second state variable to a fuzzy set created according to a predetermined rule; and a probability calculation section that calculates a probability value indicating accuracy of the passage target position based on the third state variable.

12. The endoscope system according to claim 11, wherein an amount of movement when the distal end portion is brought closer to the passage target position is set as one according to a magnitude of the probability value.

13. The endoscope system according to claim 12, wherein the amount of movement is an amount of bending per unit time of the insertion portion.

14. An endoscope system comprising:

an image pickup section that moves inside a subject to be examined and acquires an image of an object in the subject to be examined;

a probability calculation section that calculates, for each pixel of the image, a plurality of kinds of probability values accuracies of which as a passage target position of the image pickup section are evaluated based on viewpoints different from one another, at least based on a result of extraction of a dark region in the image picked up by the image pickup section and a result of calculation of a moving speed of the image pickup section; and a position setting section that performs calculation for integrating the plurality of kinds of probability values calculated by the probability calculation section, for each pixel of the image, and further sets a pixel position at which a value obtained by the calculation is the highest, as the passage target position.

15. The endoscope according to claim 14, wherein the probability calculation section calculates, for each pixel of the image, a plurality of kinds of probability values accuracies of which as a passage target position of the image pickup section are evaluated based on viewpoints different from one another, based on the result of extraction of the dark region in the image picked up by the image pickup section, the result of calculation of the moving speed of the image pickup section, and a result of detection of posture of the object to be examined.

16. An endoscope system comprising:

an endoscope provided with an insertion portion inserted into a body cavity of a subject to be examined and an image pickup section provided at a distal end portion of the insertion portion to be acquire an image of an object in the body cavity;

a probability calculation section that calculates, for each pixel of the image, a plurality of kinds of probability values accuracies of which as a passage target position of the distal end portion are evaluated based on viewpoints different from one another, at least based on a result of extraction of a dark region in the image picked up by the image pickup section, a result of calculation of a moving speed of the image pickup section, and a result of a detection of a position and an orientation of the distal end portion; and a position setting section that performs calculation for integrating the plurality of kinds of probability values calculated by the probability calculation section, for each pixel of the image, and further sets a pixel position at which a value obtained by the calculation is the highest, as the passage target position.

17. The endoscope system according to claim 16, wherein the probability calculation section calculates, for each pixel of the image, a plurality of kinds of probability values accuracies of which as a passage target position of the distal end portion are evaluated based on viewpoints different from one another, based on the result of extraction of the dark region in the image picked up by the image pickup section, the result of calculation of the moving speed of the image pickup section, a result of detection of posture of the object to be examined, and the result of the detection of the position and the orientation of the distal end portion.

18. The endoscope system according to claim 16, further comprising a bending control section that performs control for allowing the distal end portion to pass the passage target position set by the position setting section by bending the insertion portion.

* * * * *